United States Patent [19]

Yehl et al.

[11] Patent Number: 4,911,737
[45] Date of Patent: Mar. 27, 1990

[54] APPARATUS AND METHOD FOR ENVIRONMENTAL MODIFICATION

[75] Inventors: James E. Yehl; Rex R. Coppom, both of Boulder, Colo.

[73] Assignee: American Environmental Systems, Inc., Boulder, Colo.

[21] Appl. No.: 138,143

[22] Filed: Dec. 28, 1987

[51] Int. Cl.[4] ............................................. B03C 1/00
[52] U.S. Cl. .......................................... 55/2; 55/124;
55/131; 55/138; 55/139; 55/154; 98/2.11;
361/231
[58] Field of Search ..................... 55/2, 131, 149, 154,
55/155, 139, 385 R, 138, DIG. 35, 124–126;
361/231, 232, 230, 233–235; 98/2.11;
128/202.25; 2/6, 422, 410

[56] References Cited

U.S. PATENT DOCUMENTS

| | | | |
|---|---|---|---|
| Re. 27,027 | 1/1971 | Cristofv et al. ................ | 361/231 X |
| 2,060,842 | 11/1936 | Yaglou ............................. | 55/2 X |
| 2,184,644 | 12/1939 | Homberger . | |
| 2,264,495 | 12/1941 | Wilner ............................. | 361/231 |
| 2,639,972 | 5/1953 | Hicks ............................... | 361/231 X |
| 3,096,762 | 7/1963 | Winchell ......................... | 128/202.25 |
| 3,483,672 | 12/1969 | Jahnke ............................. | 55/149 X |
| 3,531,150 | 9/1970 | Jahnke ............................. | 55/2 X |
| 3,541,390 | 11/1970 | Jahnke ............................. | 55/2 X |
| 3,583,754 | 6/1971 | Von Berckheim ............... | 55/2 X |
| 3,662,217 | 5/1972 | Von Berckheim ............... | 361/231 |
| 3,678,337 | 7/1972 | Grauvogel ....................... | 361/231 |
| 3,680,281 | 8/1972 | Jahnke et al. . | |
| 3,711,743 | 1/1973 | Bolasny ........................... | 361/231 |
| 3,894,852 | 7/1975 | Von Berckheim . | |
| 4,271,452 | 6/1981 | Lee .................................. | 361/231 |
| 4,493,247 | 1/1985 | Wachsman ...................... | 361/231 X |
| 4,528,612 | 7/1985 | Spengler . | |
| 4,542,434 | 9/1985 | Gehlke et al. ................... | 361/231 |
| 4,713,724 | 12/1987 | Voelkel ............................ | 361/231 |
| 4,722,747 | 2/1988 | Armbruster ..................... | 98/2.11 X |
| 4,733,605 | 3/1988 | Holter et al. .................... | 98/2.11 |
| 4,757,422 | 7/1988 | Bossard et al. .................. | 361/231 |
| 4,811,159 | 3/1989 | Foster .............................. | 361/231 |

FOREIGN PATENT DOCUMENTS

| | | | |
|---|---|---|---|
| 1040379 | 10/1958 | Fed. Rep. of Germany ........ | 55/154 |
| 2416805 | 10/1975 | Fed. Rep. of Germany ........ | 98/2.11 |
| 2713675 | 10/1978 | Fed. Rep. of Germany ........ | 55/139 |
| 1167053 | 10/1969 | United Kingdom . | |
| 1218711 | 1/1971 | United Kingdom ................. | 98/2.11 |

Primary Examiner—Bernard Nozick
Attorney, Agent, or Firm—Robert E. Harris

[57] ABSTRACT

A compact environmental modification apparatus and method are disclosed for selectively supplementing predetermined characteristics of substantially enclosed environments, for example in rooms, and/or vehicles, to thereby more nearly simulate desirable naturally occurring environmental conditions, and to enhance the performance and/or physical and mental well-being of occupants of the enclosed environment. The apparatus preferably includes operator regulated negative ion and electrostatic field generators, as well as an electrostatic field pulsator for establishing, and regulating the frequency of, pulsations in the electrostatic field, and the apparatus may be incorporated with a system for environmental modification which includes filters for filtering of air circulated through the enclosed environment. The apparatus is particularly well adapted for convenient and advantageous location in vehicles, including, but not limited to, ground craft, aircraft, spacecraft, marine craft. and the like, and/or for location within helmets which operators and/or occupants thereof may be required to wear.

19 Claims, 5 Drawing Sheets

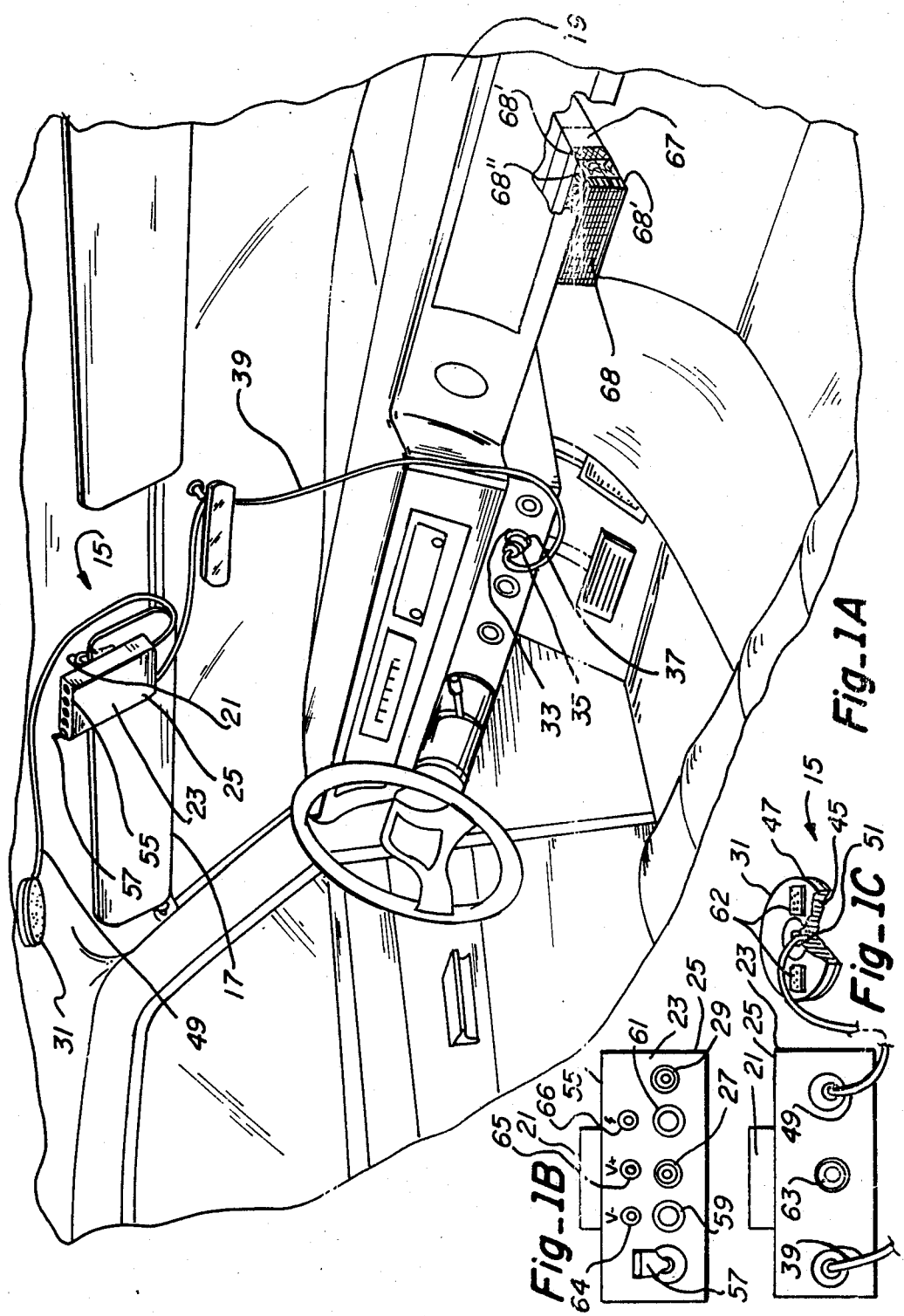

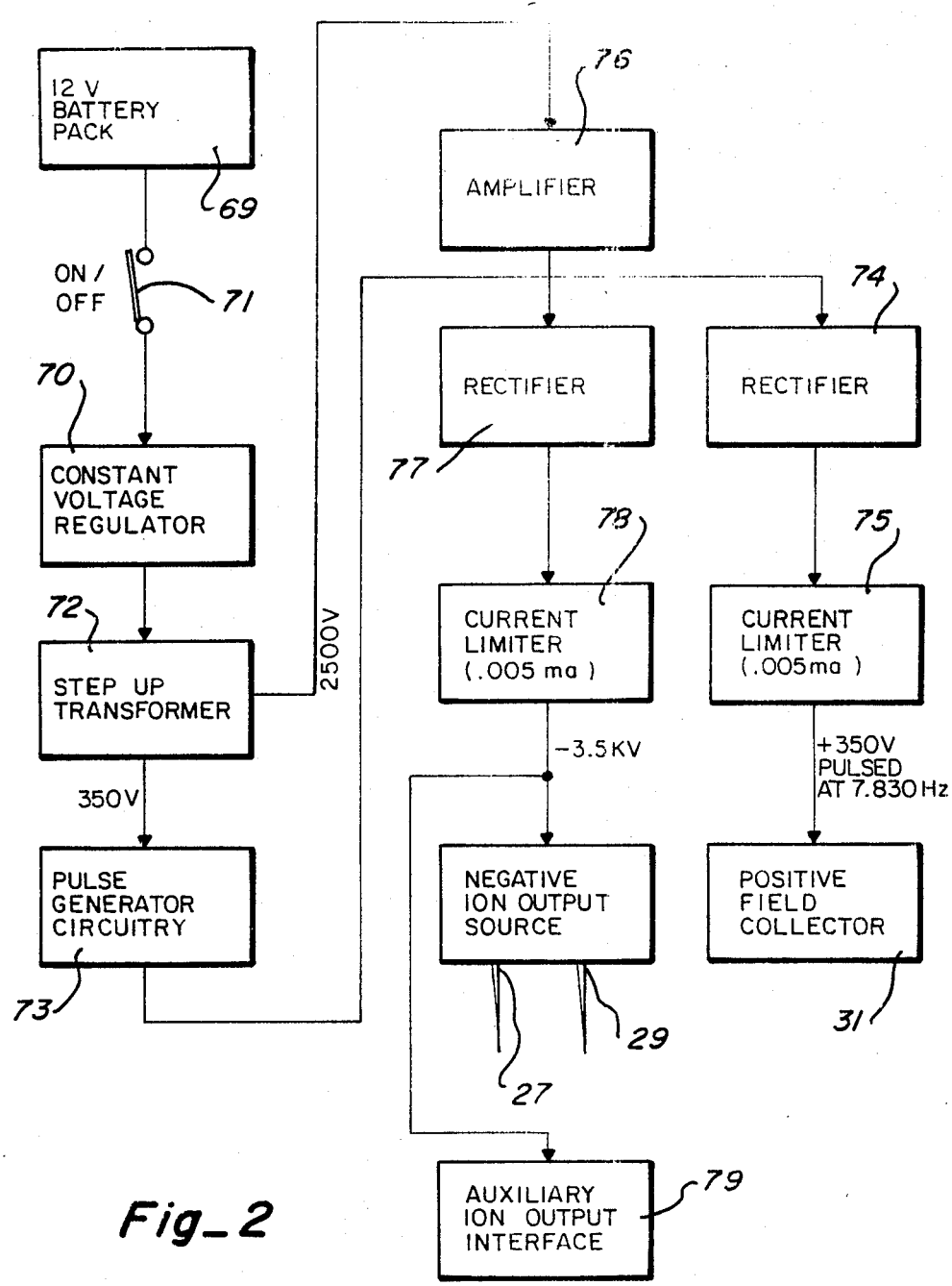
Fig_2

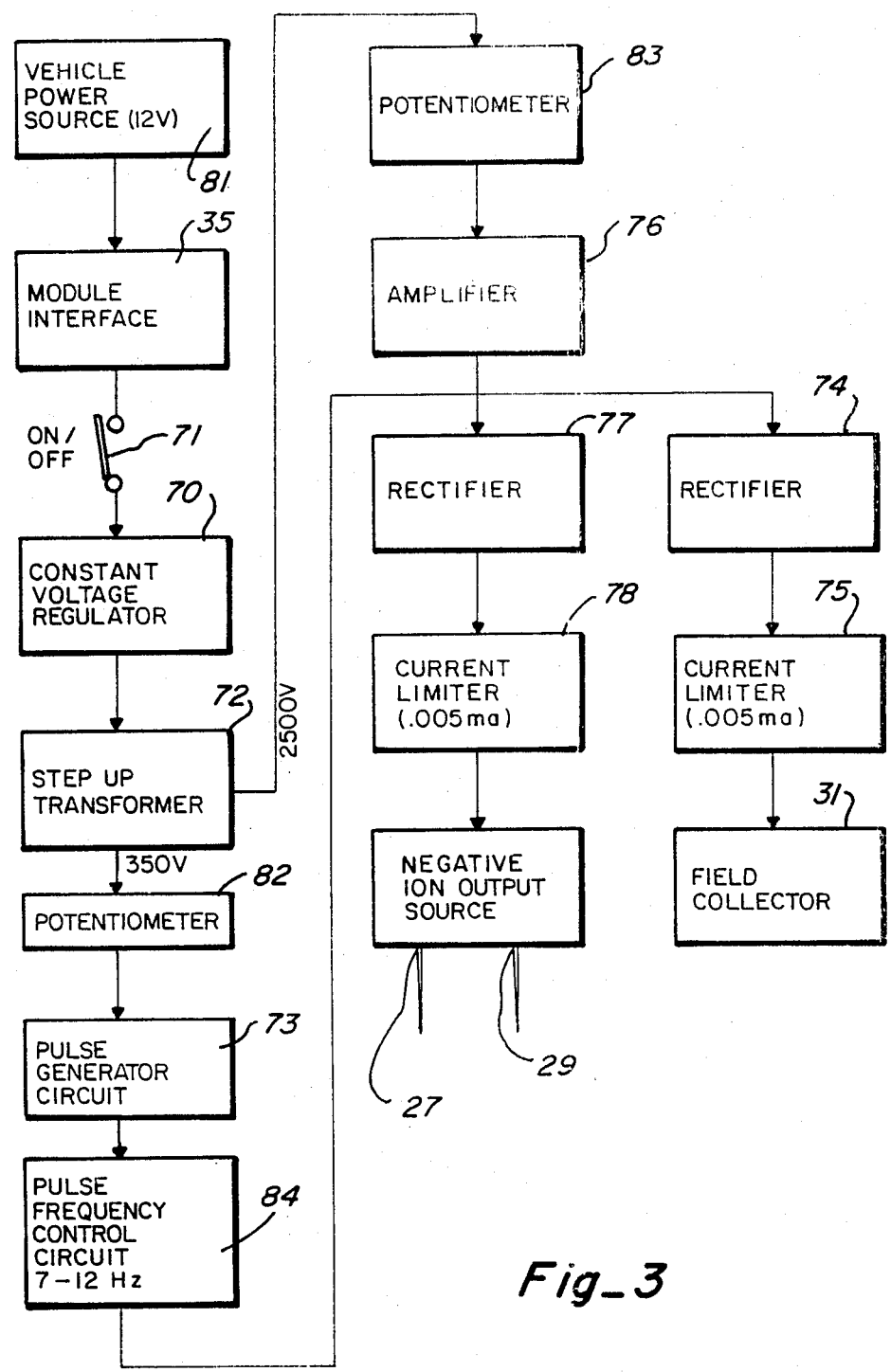
Fig_3

U.S. Patent   Mar. 27, 1990   Sheet 5 of 5   4,911,737
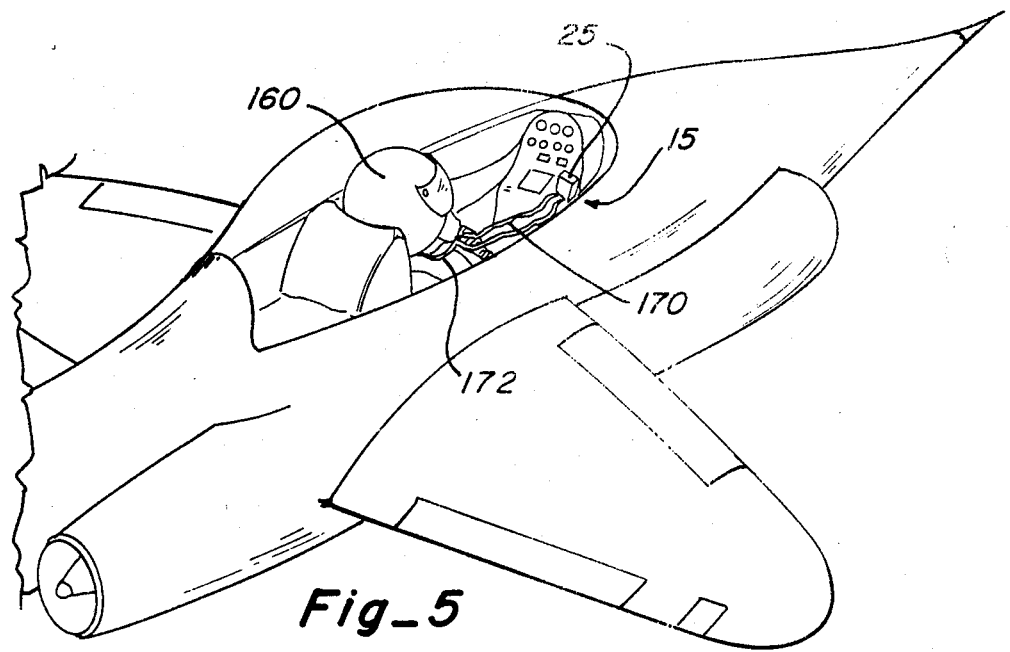
Fig_5
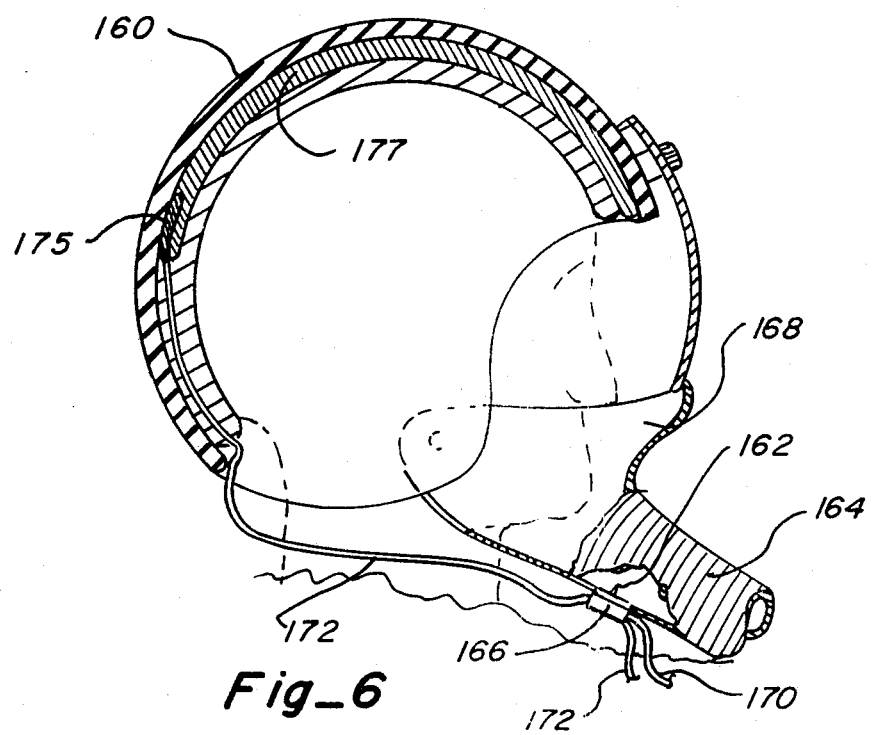
Fig_6

APPARATUS AND METHOD FOR ENVIRONMENTAL MODIFICATION

FIELD OF THE INVENTION

This invention relates to environmental modification apparatus and methods and, more particularly, relates to apparatus and methods for selectively supplementing ion content and electrostatic field characteristics of enclosed environments.

BACKGROUND OF THE INVENTION

Devices for ameliorating certain adverse characteristics of interior environments to enhance the well being of occupants thereof are known and have heretofore included means for generating ions and for purification of air (see for example U.S. Pat. Nos. 4,542,434, 4,528,612, 4,493,247, 4,271,452, 3,662,217, 1,167,053, and Re. 27,027).

Devices are also known for provision of an electrostatic field, and/or for establishing disturbances, or pulses, in an electrostatic field within such environments (see for example U.S. Pat. Nos. 4,271,452, 3,894,852, 3,680,281, 3,678,337, 3,662,217, 3,541,390, 3,531,150, 3,483,672, 2,184,644, 1,167,053, and Re. 27,027).

Indoor, or enclosed, environments have long been believed to shield occupants thereof from naturally occurring and beneficial electric fields which exist near the earth from 50 to 750 volts per meter, a phenomenon known as the Faraday Cage Effect, as well as shielding the occupants from the pulsed resonance within such naturally occurring fields (commonly referred to as the Schumann Resonance). Such pulsating fields are believed to have positive effects on humans and have a frequency typically in a range between 7 Hz and 32 Hz (and more commonly between 7 Hz and 10 Hz). It is also believed that some such environments become ion depleted, and are, therefore, particularly susceptible to accumulation of gaseous and particulate pollutants.

It has also been suggested that provision in an enclosed environment of negative ions may stimulate biochemical reactions and/or increase the metabolic rate of those breathing the ions, and may also reduce production of the hormone serotonin that is believed to be associated with depression and fatigue. (See Yaglow, C. P., "Are Air Ions a Neglected Biological Factor?" pp 269-279, in "The Air We Breathe - A Study of Man and His Environment", Farber, S. M. and Wilson, R. H. L. Editors, Charles C. Thomas, Publisher, Springfield, Ill. (1961); Soyka, Fred, "The Ion Effect", E. E. P. Dutton Publisher (1977); Assael M., Pfeifer, Y., Sulman, F.G., "Influence of Artificial Air Ionization of the Human Electroencephalogram", Department of Applied Pharmacology, Hebrew University - Hadassah Medical School and School of Pharmacy, Jerusalem, Israel (1973); and Kreuger, A. P., Strubbe, A. E., Yost, M. G. and Reed, E. J. "Electric Fields, Small Air Ions and Biological Effects" Department of Biomedical and Environmental Health Sciences and the Naval Biosciences Laboratory, School of Public Health, Earl Warren Hall, University of California, Berkely, Calif. (1976).)

While environmental modification devices heretofore known have been provided for use in vehicles and the like, such devices have not effectively provided in a single, compact device capable of ameliorating the adverse environmental conditions experienced in enclosed environments and/or providing a combination of enhancements to the environment to offset such conditions, have not provided an apparatus which is readily controllable and positionable by occupants, and have often been cumbersome and/or unduly complicated to install, in many cases requiring modification of the interior of such vehicles for application of the devices. As may be appreciated, therefore, further improvements in such devices could be utilized.

SUMMARY OF THE INVENTION

This invention provides a compact environmental modification apparatus and method for beneficially supplementing selected characteristics of substantially enclosed environments (for example rooms, vehicles including, but not limited to, ground vehicles, aircraft, spacecraft, marine craft and the like, and helmets worn by occupants and operators of such vehicles) to thereby enhance the performance and well being of operators and occupants of the enclosed environment.

The apparatus includes a negative ion generator, an electrostatic field generator for generating a positive field, and a field pulsator, with both the generators and the pulsator preferably being controllable by an occupant of the enclosed environment to selectively determine the quantity and point of discharge of negative ions, the strength and position of the electrostatic field, and the frequency of the pulsations in the elecrostatic field. The apparatus is compact and may be permanently installed or be portable between environments. The apparatus is advantageously employed in a system for modification of interior environments including air filtration, for example, using high efficiency particulate air (HEPA) and/or activated carbon charcoal type filters.

It is therefore an object of this invention to provide an apparatus and method for supplementing predetermined characteristics of substantially enclosed environments.

It is another object of this invention to provide an apparatus and method for supplementing enclosed environments by providing negative ions, a positive electrostatic field grid, and electrostatic field pulsations within the environment.

It is still another object of this invention to provide an apparatus and method for supplementing enclosed environments by provision of negative ions, a positive electrostatic field grid, electrostatic field pulsations, and air filtration within the environment.

It is yet another object of this invention to provide a portable and compact apparatus for selectively supplementing substantially enclosed environments which is releasably attachable within the environment thus providing portability between environments.

It is still another object of this invention to provide an apparatus and method for selectively supplementing substantially enclosed environments which provides the user with the capability of selecting the quantity of negative ion output, the strength of the electrostatic field, the position of the positive field generator and collector and point of ion generation, and the frequency of the pulsations within the electrostatic field.

It is still another object of this invention to provide a compact apparatus for selectively supplementing substantially enclosed environments which is usable in vehicles such as land vehicles, aircraft, space craft, marine craft, and the like, and/or which may be used in association with the protective head gear, for example, a helmet, of an operator of such vehicles.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIG. 1A is a perspective view of a portable environmental control apparatus the control module of which is removably attachable at a preselected position in the interior of a vehicle, for example to the sun visor of an automobile, and illustrating use of the apparatus in an overall system including filtration of intake and/or recirculated air;

FIG. 1B is a front elevation view of the control module shown in FIG. 1A;

FIG. 1C is a rear elevation view of the control module shown in FIG. 1B shown in conjunction with the remotely positionable positive field collector used in the apparatus;

FIG. 2 is a block diagram of the components of a first embodiment of the portable environmental control apparatus of FIG. 1 which is operable from its own internal power source;

FIG. 3 is a block diagram of a second embodiment of the environment control apparatus of FIG. 1 operable from a 12 volt power supply system within the enclose environment and including means for controlling the output of the apparatus;

FIG. 5 is a perspective view of the compact environmental control apparatus of this invention configured for use in association with a helmet worn by the operator of an aircraft; and FIG. 6 is a sectional view of the helmet portion of the apparatus of FIG. 5.

DESCRIPTION OF THE INVENTION

Figures 4A, 4B:
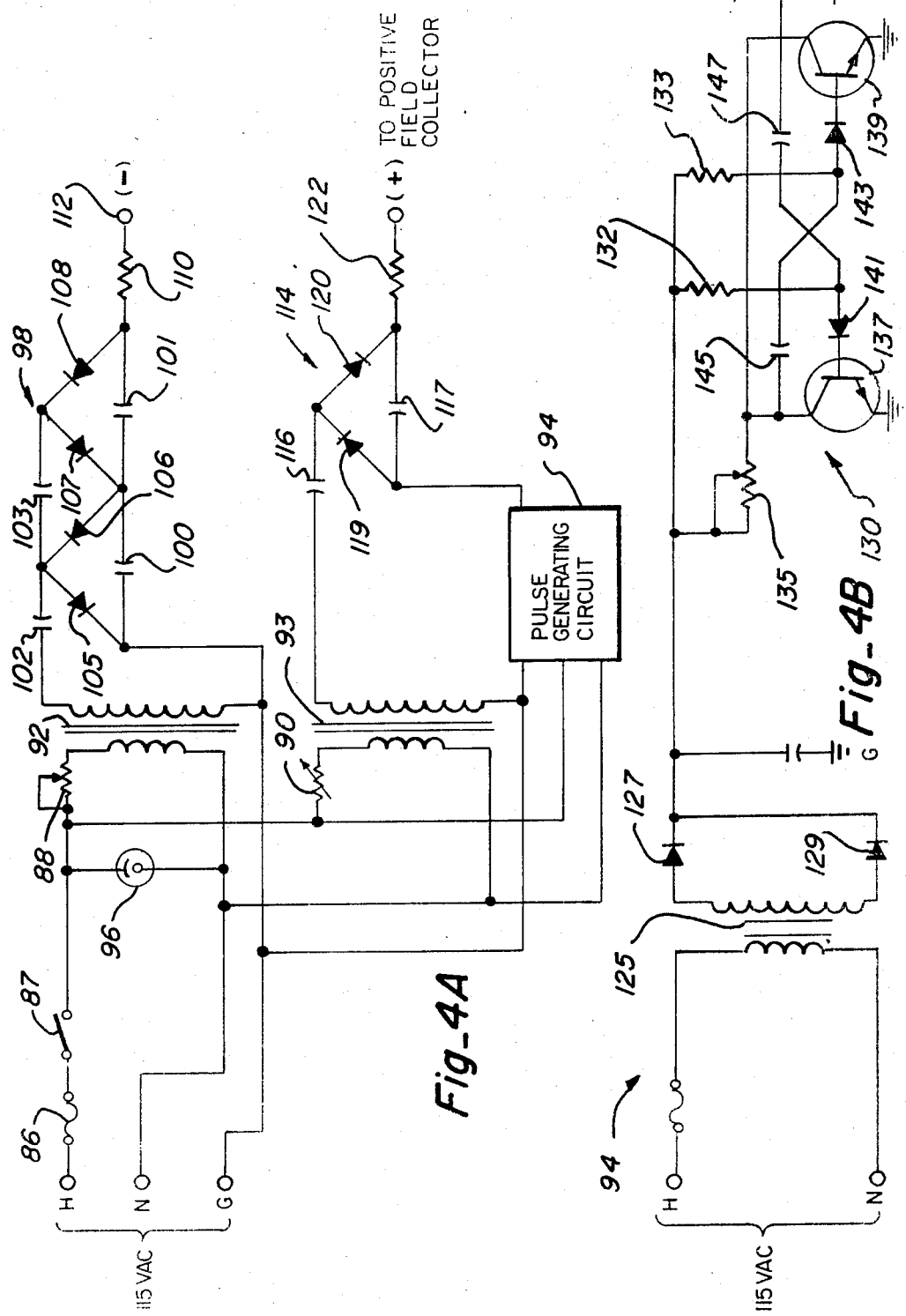
FIG. 4A is a schematic view of the components of a third embodiment of the environmental control apparatus operable from a conventional 115 volt AC power source.
FIG. 4B is a schematic view of the pulsing unit of FIG. 4A.

A first and now preferred embodiment of the invention 15 is shown in FIGS. 1A through 1C. In FIG. 1A, apparatus 15 is shown releasably attached to sun visor 17 of automobile 19 using clip 21. Clip 21 is affixed to the housing 23 of environmental control apparatus module 25, which housing contains the electronic circuitry (preferably micro-circuits) for producing negative ions at electrodes 27 and 29 (typically needle electrodes which are conventionally mounted in housing 23) and the pulsed, positive electrostatic field emanating from field collector 31. The overall module 25 is compact, typically being, for example, approximately 4 inches long, 3 ⅛ inches wide and 1 inch thick.

Apparatus 15 is connected to the 12 volt battery of automobile 19 through the cigarette lighter housing 33 using interface 35, herein comprising lighter adapted plug 37 for linking the 12 volt supply to the circuitry of module 25 through cord 39.

Positive field collector 31, as shown in FIG. 1C, includes electro-conductive carbon foam surface 45 within insulating dish housing 47, and maintained therein, for example, by nonconductive adhesive gel. Electro-conductive carbon foam surface 45 may be, for example, Ensolite CEC by Uniroyal. Collector 31 is connected to module 25 by signal supply lead 49 for coupling the voltage signal from the microcircuitry of module 25 to electro-conductive carbon foam surface 45 through electrode 51.

While module 25 is shown herein attached to the existing 12 volt battery of an automobile, it should be realized that the apparatus could make use of a variety of existing power sources in a variety of vehicles (for example land, marine, and air craft), and/or could make use of its own 12 volt battery pack as more fully set forth hereinbelow. In addition, while a 12 volt source is herein specified, it will be realized by those skilled in the art that the apparatus could be modified for use with power sources having different output voltages.

Housing 23 of apparatus 15 includes at the forward surface 55 thereof, on/off control 57, operational indicator lights 59 and 61 (indicator light 59 indicating that the ion generator is operational, and indicator light 61 indicating that the positive pulsed field is operational), as well as the negative ion generation electrodes 27 and 29.

By providing a module and field collector which may be selectively positionable within the particular enclosed environment, the point of generation of negative ions may be advantageously positioned to maximize intake of negative ions by a user of the device, and positioning of the positive field collector may also be advantageously selected for maximum effectiveness, for example above the head of the operator (or passenger) (using, for example, strips of the trade marked product Velcro 62 attached to dish housing 47). In addition, provisions may optionally be made for grounding of the operator and/or occupants, if desired.

If a more permanent positioning of the positive field collector 31 is desired, the field collector may be permanently installed (by use of screws, adhesives or the like) with cord 39 provided with a jack for attachment to a mating jack located in housing 23. In addition, an additional outlet receptacle 63 for provision of an additional, remote ion electrode may be provided in module housing 23. Hand-manipulable control knobs 64, 65 and 66 (as shown in FIG. 1B) may be provided at the forward surface 55 of housing 23 for adjustment of negative ion output, positive electrostatic field strength, and the frequency of pulsations provided within the field respectively (as described hereinbelow).

Air intake and/or recirculation ducts (for example duct 67) may have filters (for example filter 68) positioned therein to thereby provide filtering of particulates and gases otherwise present in the environment. The filter system is preferably a combination of a 0.3 micron high efficiency particulate air (HEPA) filter 68' and an activated carbon charcoal filter 68''.

Turning now to FIG. 2, one embodiment of a circuitry for apparatus 15 is shown, with the apparatus being operable from its own 12 volt battery pack 69. The +12 DC voltage supplied from battery pack 69 is received by constant voltage regulator 70 upon activation of on/off switching mechanism 71. Constant voltage regulator 70 (for example a 12 volt Zener diode) provides a steady +12 volt signal which is received by DC step-up transformer 72, the secondary coil of which is center tapped, providing a 350 volt signal at one output and a 2,500 volt signal at the other output. The 350 volt signal is received by pulse generator 73 the output signal of which is pulsed at a frequency of about 7.830 Hz. Pulse generator 73 is connected with rectifier 74. The positive portion of the pulsed 350 volt signal is thereafter received at current limiter 75 for limiting the current of the signal to about 0.005 mA at positive field collector 31.

The 2500 volt signal from step-up transformer 72 is received at amplifier 76 where the signal is amplified providing a 3.5 KV signal which is rectified at rectifier 77. The negative portion of the signal is received at current limiter 78 (limiting signal current to 0.005 mA) and thereafter at electrodes 27 and 29 as well as auxiliary ion output interface 79.

A second embodiment of the circuitry of apparatus 15 is shown in FIG. 3 and includes interface 35 attachable to a 12 volt power source 81 already existing within the particular enclosed environment. As indicated in FIG. 3, the DC signal provided at interface 35 is coupled through switch 71 and constant voltage regulator 70 to DC step-up transformer 72 which is connected with pulse generator circuitry 73 and amplifier 76 as was previously described in FIG. 2. However, the output signals from transformer 72 are connected to potentiometers 82 and 83, potentiometer 82 allowing user regulation of the intensity of the electrostatic field produced at field collector 31, preferably within a range from 0 to 350 volts, and potentiometer 83 allowing control over voltage supplied to the negative ion output sources 27 and 29 in a range from 1.5 KV to 3.5 KV thereby allowing user regulation of the quantity of negative ions produced at the electrodes.

Pulse frequency control circuit 84 is connected between pulse generator 73 and potentiometer 83 for providing user control of the frequency of the pulses within the electrostatic field in a range from 7 to 32 Hz (preferably from 7 Hz to 12 Hz), which range corresponds with the naturally occurring pulsations in the electrostatic field surrounding the earth commonly referred to as the Schumann resonance.

While user controls for control of ion output, electrostatic field strength and frequency of field pulsations are shown in FIG. 3, it should be realized that control over less than all of the above parameters may be desirable in any particular embodiment of the invention, those parameters without such user control being set for a predetermined output in a desirable range as heretofore discussed.

Referring now to FIGS. 4A and 4B, the circuitry for another embodiment of the apparatus is shown for use in association with a conventional 115 volt AC power supply. The 115 volt signal is coupled through fuse 86 and switch 87 to potentiometer 88 and variable resistor 90. Potentiometer 88 is connected to step-up transformer 92 for stepping the voltage up to 1200 volts. Variable resistor 90 is connected to step-up transformer 93 for separately stepping up the voltage output from the secondary coil thereof to 1000 volts The 115 volt signal is also provided to pulse generating circuitry 94 for providing a pulsed output having a frequency of between 7 and 12 Hz (as more fully illustrated in FIG. 4B). Indicator lamp 96 is provided for indicating operability of the apparatus upon closure of switch 87.

The output from transformer 92 is connected with amplifier and rectifier circuitry 98 for providing a rectified signal therefrom having a user controlled voltage of between 0 and −9 KV. Amplifier and rectifier circuitry 98 is a conventional circuit and includes capacitors 100, 101, 102 and 103, diodes 105, 106, 107 and 108 and resistor 110. The amplified and rectified voltage signal is supplied to negative ion output source 112 for adjustable negative ion output thereat.

The output from transformer 93 is connected to amplifier/rectifier circuitry 114, as is pulse generating circuitry 94. Amplifier and rectifier circuitry 114 includes capacitors 116 and 117 and diodes 119 and 120 in a conventional configuration, and is connected through resistor 122 to a positive field collector as previously set out herein. Variable resistor 90 enables user control over the intensity of the positive electrostatic field produced at the field collector in a range from 0 to +3.2 KV.

FIG. 4B illustrates in detail adjustable frequency pulse generating circuitry 94 overall operation of which effectively establishes a ground interrupt system for establishing and regulating pulsations in the positive electrostatic field. The 115 volt AC signal is received at step-up transformer 125 (preferably producing an output matching that of transformer 93) the opposite sides of the secondary coil of which are connected to diodes 127 and 129 for full wave rectification of the signal. The DC output from the diodes is connected to pulse producing circuit 130 which includes resistors 132 and 133 and potentiometer 135. The DC signal is received at the bases of transistors 137 and 139 through resistors 132 and 133 and diodes 141 and 143, and is received at the collectors of transistors 137 and 139 through potentiometer 135 (for control over frequency of pulsations). The emitters of transistors 137 and 139 are connected to ground. Capacitor 145 is connected between the collector of transistor 137 and the junction of the base of transistor 139 (through diode 143) and resistor 133. The out signal from circuit 130 is received at amplifier/rectifier circuitry 114 through capacitor 147.

FIGS. 5 and 6 illustrate an embodiment of apparatus 15 wherein module 25 may include circuitry substantially similar to the circuitry shown in FIGS. 2 or 3. As shown in FIG. 5, however, module 25 is used in connection with helmet 160 (herein shown to be a helmet typical of those which may be used by aviators and the like).

As shown in FIG. 6, helmet 160 is provided with negative ion electrode 162 adjacent air intake nozzle 164, with the electrode being provided in insulating housing 166. By provision of the negative ion output at the point of attachment of nozzle 164 to mask 168, the user of helmet 160 maximizes intake of negative ions. Of course, when the apparatus of this invention is used in association with a helmet having no such air intake system and/or face mask, the position of the negative ion output electrode may still be selectively located, as set forth in FIG. 1 for example.

Signal supply line 170 is provided between electrode 162 and module 25. A second signal cord 172 from module 25 is provided at the rear of helmet 160 (and may include a jack and plug arrangement for disengagement of the line from the helmet) for connection to electrode 175 in electro-conductive carbon foam surface 177. In this fashion, the positive electrostatic field is provided at the electro-conductive carbon foam surface 177 within helmet 160. In other regards, the circuitry of module 25 is substantially similar to that shown in FIGS. 2 and 3, and provides for the output of negative ions and a positive electrostatic field which is pulsed within the 7 to 32 Hz range, and which may also include user controls for controlling the frequency of pulsations, the intensity of the electrostatic field, and the quantity of negative ion output.

As may be appreciated from the foregoing, this invention provides an improved, compact environmental modification apparatus for supplementing predetermined characteristics of substantially enclosed environments to enhance the performance and physical and mental well-being of occupants thereof, which apparatus may be portable, selectively positionable for achieving the most advantageous position for negative ion output and pulsed electrostatic field generation with respect to a user of the apparatus, and which may provide for user control within predetermined parameters of one or more of the quantity of negative ions generated and the intensity of, and frequency of pulsations in, the electrostatic field.

I claim:

1. A compact apparatus for modification of preselected characteristics of a substantially enclosed environment, said apparatus comprising:
   voltage supply means adapted to be connected with a voltage source;
   ion generating electrode means connected with said voltage supply means for generation of ions within the substantially enclosed environment;
   field collector means connected with said voltage supply means and spaced from said ion generating electrode means for establishing an electrostatic field within the substantially enclosed environment;
   pulsating means connected with said voltage supply means and said field collector means for generating pulsations in said electrostatic field at said field collector means;
   level control means for controlling generation of ions at said ion generating electrode means and generation of said electrostatic field at said field collector means; and
   compact and portable housing means for mounting said ion generating electrode means and said level control means thereon, and for housing said voltage supply means and said pulsating means, said housing means including releasable attachment means configured for releasably attaching said housing means to selected structure within the substantially enclosed environment without requiring modification or supplementation of said structure of the substantially enclosed environment to accommodate attachment thereto, whereby preselected characteristics of the substantially enclosed environment are modified to more nearly establish predetermined naturally occurring environments and said apparatus is portable between different such environments.

2. The apparatus of claim 1 wherein said level control means also includes frequency regulating means for regulating the frequency of pulsations generated by said pulsating means in said electrostatic field in a range from 7 Hz to 32 Hz.

3. The apparatus of claim 1 wherein said substantially enclosed environment is defined by a mobile structure, wherein said apparatus is variably positionable in said mobile structure for optimal positioning of said ion generating electrode means with respect to occupants of said mobile structure, wherein said field collector means establishes a positive field, and wherein said field collector means has an electroconductive carbon foam surface.

4. The apparatus of claim 1 wherein said substantially enclosed environment is defined by a mobile structure, wherein said apparatus is used in association with a protective head gear worn by an occupant of the mobile structure, wherein said ion generating electrode means generates negative ions and is adjacent to said protective head gear, wherein said field collector means is positionable in the protective head gear, and wherein said pulsating means establishes pulsations in said electrostatic field having a frequency of between 7 Hz and 12 Hz.

5. The apparatus of claim 1 wherein said level control means includes means for varying the quantity of ions generated by said ion generating electrode means, and wherein said ions are negative ions.

6. The apparatus of claim 2 wherein said field collector means establishes a positive electrostatic field and wherein said level control means includes intensity control means for varying the intensity of said positive electrostatic field.

7. A system for selective modification of preselected characteristics of a substantially enclosed environment to more nearly establish predetermined naturally occurring environments therein, said system comprising:
   voltage supply means adapted to be connected with a voltage source;
   electrode means connected with said voltage supply means to generate a selected quantity of ions within said environment;
   field collector means connected with said voltage supply means to generate a selected electrostatic field intensity within said environment, said electrostatic field intensity and said quantity of ions generated being selectable independently of one another; and
   pulsating means for pulsating said electrostatic field at said field collector means at a selected frequency.

8. The system of claim 7 wherein said system includes voltage varying means connected with said voltage supply means whereby said voltage supplied to said field collector means is variable in a range from 0 volts to +350 volts.

9. The system of claim 7 wherein said pulsating means causes selection of the frequency of said pulsations in said electrostatic field in a range from 7 Hz to 12 Hz.

10. The system of claim 7 wherein said system includes voltage varying means connected with said voltage supply means whereby said voltage supplied to said electrode means is variable in a range between 0 volts and −3.5 kilovolts.

11. The system of claim 10 wherein said electrode means includes first and second electrodes.

12. The system of claim 7 wherein the substantially enclosed environment is a vehicle and wherein said system further includes first and second releasable attachment means for releasably attaching said electrode means and said field collector means at selected locations within the vehicle.

13. The system of claim 7 wherein said field collector means includes polarity reversing means for reversing the polarity of said electrostatic field generated at said field collector means.

14. The system of claim 7 wherein said field collector means includes an electro-conductive carbon foam portion, and wherein the substantially enclosed environment is subject to movement so that an occupant thereof normally wears a helmet, said electrode means and said electroconductive carbon foam portion of said positive field collector being positioned adjacent to said helmet.

15. The system of claim 7 further comprising air filtration means for filtration of air in the enclosed environment, said air filtration means including at least one of a high efficiency particle accumulator and an activated carbon charcoal filter, whereby air is, in cooperation with said electrode means and said field collector means, further cleansed thus enhancing air quality in the substantially enclosed environment.

16. A method for selective modification of preselected characteristics of a substantially enclosed environment to more nearly establish predetermined naturally occurring environments therein, said method comprising:

generating a selected quantity of ions within said environment by applying voltage to electrode means so that ions are produced thereat;
generating an electrostatic field within said environment by applying voltage to field collector means to thereby provide a selected electrostatic field intensity within said environment, said electrostatic field intensity and said quantity of ions generated being selectable independently of one another; and
pulsating said electrostatic field at said field collector means at a selected frequency.

17. The method of claim 16 wherein said enclosed environment is a vehicle, and wherein said method further comprises generating said ions and generating said electrostatic field at occupant selected first and second positions, respectively, within the vehicle.

18. The method of claim 16 wherein said method further comprises generating said ions and generating said electrostatic field within a helmet.

19. The method of claim 16 wherein said step of generating ions includes providing means for generating negative ions, wherein said electrostatic field established is a positive electrostatic field, and wherein said pulsations established within said field have occupant frequency of between 7 Hz and 32 Hz.

* * * * *

UNITED STATES PATENT AND TRADEMARK OFFICE
CERTIFICATE OF CORRECTION

PATENT NO. : 4,911,737
DATED : March 27, 1990
INVENTOR(S) : Yehl et al.

It is certified that error appears in the above-identified patent and that said Letters Patent is hereby corrected as shown below:

Column 3, line 37, "enclose" should be --enclosed--.

Column 4, line 62, "68'" should be --68''--.

Column 6, line 46, after "with" insert --a protective head gear, for example--.

Column 8, line 20, "2" should be --5--.

Column 10, line 24, after "have" insert --an--.

Column 10, line 24, after "occupant" insert --selectable--.

Signed and Sealed this

Nineteenth Day of November, 1991

Attest:

HARRY F. MANBECK, JR.

*Attesting Officer*         *Commissioner of Patents and Trademarks*